United States Patent [19]

Di Ianni et al.

[11] Patent Number: 5,180,677
[45] Date of Patent: Jan. 19, 1993

[54] LYSING REAGENT FOR LEUKOCYTE DIFFERENTIATION METHOD

[75] Inventors: Ludmilla P. Di Ianni, Hawthorne, N.J.; Edward L. Carver, Jr., Oxford, Conn.

[73] Assignee: Fisher Scientific Company, Pittsburgh, Pa.

[21] Appl. No.: 215,396

[22] Filed: Jul. 5, 1988

[51] Int. Cl.⁵ ............................................. G01N 31/00
[52] U.S. Cl. ......................................... 436/17; 436/8; 252/408.1
[58] Field of Search ..................................... 436/8–18; 252/408.1

[56] References Cited

U.S. PATENT DOCUMENTS

| | | | |
|---|---|---|---|
| 4,389,490 | 6/1983 | Crews et al. | 436/17 |
| 4,521,518 | 6/1985 | Carter et al. | 436/17 |
| 4,656,139 | 4/1987 | Matsuda et al. | 436/17 |

OTHER PUBLICATIONS

"Physical and Chemical Characteristics of Armak Quaternary Ammonium Salts" Product Data Bulletin 81-6, *Armak Corp.*, 1981.

*Primary Examiner*—James C. Housel
*Assistant Examiner*—William Chan
*Attorney, Agent, or Firm*—Alan M. Doernberg

[57] ABSTRACT

A lysing reagent is employed for stromatolysing the red cells in a blood sample and differentiating the leukocytes into subpopulations. The lysing reagent contains a dodecyltrimethylammonium halide and an aromatic second cationic agent which is either a benzyltrialkylammonium halide or an alkylpyridinium halide. In some methods, the lysing reagent is mixed in the reaction chamber with a major proportion of the diluent, and the blood sample with a minor proportion of the diluent is added to the reaction chamber.

25 Claims, 2 Drawing Sheets

LYSING REAGENT FOR LEUKOCYTE DIFFERENTIATION METHOD

The present invention relates to hematology reagents and methods for lysing red cells and causing white cells (leukocytes) to differentiate in size into subpopulations.

Lysing reagents containing at least one quaternary ammonium salt wherein the nitrogen is attached to four alkyl groups (three short such as methyl, one long such as alkyl of 12–16 carbons) have been used in the white cell/hemoglobin channel of automated hematology analyzers. See U.S. Pat. Nos. 3,874,852 (1975), 4,286,963 (1981), 4,346,018 (1982), 4,485,175 (1984), 4,521,518 (1985) and 4,528,274 (1985). In each such case, the lysing reagent is mixed with a mixture of diluent and blood sample to create a reaction mixture in which the red cells are stromatolyzed and the liberated hemoglobin converted to cyanmathemoglobin by cyanide in the lysing reagent. In the latter five of these patents, various mixtures of such quaternary ammonium salts are employed for the purpose of having the leukocytes in the blood sample not merely shed their cytoplasm to form an undifferentiated population of cell nuclei, but rather to lose their cytoplasm in a fashion that differentiates between types of leukocytes.

For clinical evaluation purposes, there are five types of leukocytes: lymphocytes, basophils, eosinophils, monocytes and neutrophils. Early methods employing mixtures of quaternary ammonium salts sought to obtain a value for total leukocytes and a proportion thereof which were lymphocytes. Later methods (see especially U.S. Pat. No. 4,485,175) sought to differentiate leukocytes into three populations: lymphocytes, mononuclear cells and neutrophils; the intention in such methods is to have basophils, eosinophils and monocytes all be counted as mononuclear cells or as being within the mononuclear region of about 105 to 200 femptoliters In actual practise, an attempt has also been made to identify abnormal distributions of subtypes within the mononuclear region without actual quantitation of basophils, eopinophils and monocytes In addition, the term "neutrophils" has been adopted for those cells showing an impedance value larger that about 200 femptoliters, which normally includes all of the neutrophils and sometimes includes some of the eosinophils.

U.S. Pat. No. 4,617,275 (1986) describes a lysing reagent used to obtain three-part differentiation without containing cyanide for hemoglobin determination Such reagent is employed in a TOA instrument which has a third channel for hemoglobin determination The lysing reagent contains two quaternary ammonium cationic agents (one of which is dodecyltrimethylammonium chloride as in U.S. Pat. Nos. 4,346,018 and 4,485,175) and contains citric acid. The second quaternary ammonium cationic agent is either tetradecyltrimethylammonium bromide or hexadecyltrimethylammonium chloride (both of which are mentioned as second cationic agents in the other patents).

U.S. Pat. No. 4,528,274 (1985) describes lysing reagents which contain, in addition to the two cationic agents, a third surfactant which is either non-ionic or anionic. It is believed that such agent may, in fact, be present for the purpose of neutralizing the strong lytic activity of impurities found in the cationic agents used (especially in Arquad 12/50).

As evidenced by U.S. Pat. Nos. 4,617,275 and 4,528,274, recent efforts to improve the diffentiation activity of hematology lysing reagent has focused upon ingredients additional to two cationic agents. The cationic agents themselves have been standardized as being dodecyltrimethyl ammonium chloride and an alkyltrimethylammonium halide wherein the alkyl is of 14 to 16 carbons (tetradecyl or hexadecyl).

BRIEF DESCRIPTION OF THE INVENTION

The present invention is based upon the use, in lysing reagents for hematological analysis including leukocyte differentiation, of certain aromatic cationic agents of two classes: benzyltrialkylammonium halides (where the two of the alkyls are methyl or ethyl, preferably methyl, and the third alkyl is of 14 to 16 carbons) and alkylpyridinium halides (where the alkyl is of 14 to 16 carbons). Accordingly, the present invention includes an improved lysing reagent for use in automated hematological measurement containing dodecyltrimethylammonium halide and a second cationic agent, characterized by the second cationic agent being selected from the group consisting of benzyltrialkylammonium halides of the formula:

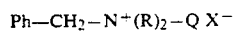

and alkylpyridinium halides of the formula:

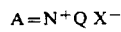

wherein Ph is phenyl, R is methyl or ethyl, Q is alkyl of 14 to 16 cabons, A=N is pyridinium and X is chlorine or bromine.

The present invention further includes an improved method for stromatolyzing a blood sample with a mixture of cationic agents to produce a reaction mixture in which the leukocytes have been differentiated by size into subpopulations, with one of the cationic agents being a dodecyltrimethylammonium halide, characterized by another of the cationic agents being selected from the group consisting of such benzyltrialkylammonium halides and such alkylpyridinium halides.

BRIEF DESCRIPTION O THE DRAWING

DETAILED DESCRIPTION OF THE INVENTION

Figure 1:
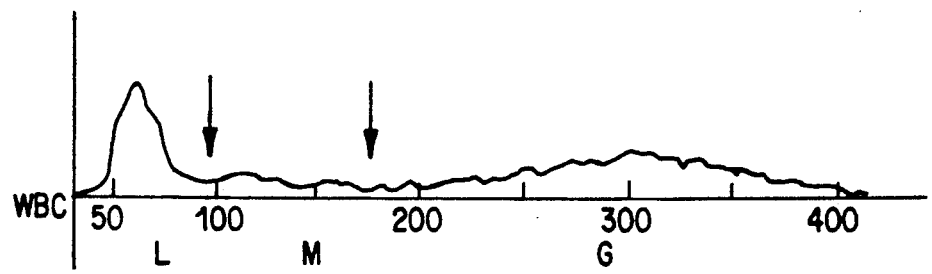
FIG. 1 is a graphic view of a histogram using a lysing reagent in accordance with the present invention on a coulter S Plus IV instrument as described in Example 1.

The lysing reagent employed in the present invention contains, at minimum, at least two cationic agents. In the preferred case wherein the reaction mixture will also be used to obtain a hemoglobin measurement, the lysing reagent will also contain a cyanide salt such as potassium cyanide. Non-ionic and anionic materials, such as citric acid and the non-ionic and anionic surfactants described in U.S. Pat. No. 4,528,274 may be present, but are not preferred. The lysing reagent is used in combination with an isotonic diluent, which may be of the composition described in U.S. Pat. No. 4,346,018, but is preferably based upon organic buffers other than ADA.

The first cationic agent present in the lysing reagent is a dodecyltrimethylammonium halide, preferably the chloride. It is preferred to use the dry form of this compound which is relatively free of higher homologs. The liquid form of this product (such as Arquad 12/50) contains variable amounts of higher homologs (such as the corresponding tetradecyl and hexadecyl compounds) which act as strong lysing reagents Variability in such impurities is believed to impart too rapid removal of the cytoplasm of leukocytes, with resultant shift of the size pattern towards smaller counted particles. In the less preferred case where such impure dodecyltrimethylammonium chloride is employed, additives may be helpful in neutralizing such activity.

The second cationic agent may be either a benzyl compound or a pyridinium compound. If it is a benzyl compound, then Q of the above first formula can be alkyl of 14-16 carbons, such as tetradecyl or hexadecyl, but is preferably tetradecyl. R in such formula can be methyl or ethyl (or one of each), but is preferably methyl. X in such formula can be chlorine or bromine (so that the compound is a chloride or bromide), but is preferably chloride. Thus the preferred benzyl cationic agent is benzyltetradecyldimethylammonium chloride (referred to hereafter as BeTDMAC)

If the second cationic agent is a pyridinium compound, then Q of the above second formula can be alkyl of 14-16 carbons, such as tetradecyl or hexadecyl. X can be chlorine or bromine, but is preferably chlorine.

In both cases, the chain length of Q is believed responsible for the type of activity of the cationic agent. If Q were of 12 carbons, it is believed that the agent would have insufficient lytic activity to completely stromatolyze the red cells. A formulation that was prepared using dodecylpyridinium chloride suffered from this deficiency If Q were of 18 carbons, it is believed that the solubility of the compound in aqueous media would be undesirably low and that the lytic activity of the compound might be too strong to retain leukocyte differentiation.

The suitable proportions of dodecyltrimethylammonium halide and either benzyl compound or pyridinium compound can be determined by routine experimentation based upon the following criteria. First, the most important concentration is that of the two agents in the final reaction mixture consisting of diluent, lysing reagent and blood sample. Since the diluent composition would normally be adjusted for optimal results on other channels (especially the red cell channel wherein a different blood sample is mixed only with diluent), the two primary variables are lysing reagent composition and dilution ratio. Depending upon the instrument, the lysing reagent may be diluted anywhere from five-fold to fifteen-fold. Within the constraints of this dilution ratio, the concentration of both cationic agents in the lysing reagent can be adjusted to achieve two effects: complete stromatolysis of the red cells and an optimal pattern of leukocyte size distribution after a suitable reaction period (generally 2 to 7 seconds before counting and 3 to 10 seconds of impedence counting). In the event that a particular formulation imparts incomplete stromatolysis, one should try raising the concentration of the second cationic agent In the event that a particular formulation has insufficient differentiation, particularly of the lymphocytes from other subpopulations, one should try lowering the concentration of the second cationic agent.

The order of addition of lysing reagent, blood sample and diluent is important to proper leukocyte differentiation, but not in the manner described in U.S. Pat. No. 4,485,175, which requires that, at the time of contact with cells, the lysing reagent be both very dilute and added very slowly. For the present method, contact of cells with strongly concentrated lysing reagent should be avoided; however, slow mixing to expose the cells to a gradient of lytic shock (from low exposure to cationic agent to highest exposure to cationic agent) is unnecessary It is, in fact, preferred to premix in the reaction chamber all of the lysing reagent and most of the diluent and then add the blood sample with the remainder of the diluent. The effect is to expose the blood initially to a reaction mixture having both cationic agents at greater than final concentration (but less than twice final concentration), with the further addition of diluent quickly bringing the concentration of both cationic agents down to final concentration.

If one wishes to evaluate a formulation outside of an automated analyzer, one should make up a first mixture of all of the lysing reagent and most of the diluent A carefully measured quantity of blood sample should be separately mixed with the remainder of the diluent. The diluted blood can then be added to first mixture and, after a reaction time determined experimentally within predetermined ranges, the complete reaction mixture placed in the counting chamber of a manual impedance instrument (such as the COULTER S instrument).

By employing the lysing reagent of the present invention, especially with partially diluted blood being added to partially diluted lysing reagent, excellent patterns of leukocyte distribution are obtainable. As indicated in the examples that follow, such patterns can include good separation between lymphoid populations (generally at 45 to 105 femptoliters impedance counting size), mononuclear populations (generally at 105 top 200 femptoliters impedance counting size) and granulocyte (neutrophil) populations (generally at greater than 200 femptoliters impedance counting size). In some instances with pyuridinium compounds, the shape of the granulocyte (neutrophil) peak is that of a rounded peak rather than the flatter peaks generally obtained with other lysing reagents. In some instances with benzyl compounds, even though the lymphoid and granulocyte peaks are rounded, the mononuclear region has one or more visible peaks in contrast to the generally flat shapes shown in the figures of U.S. Pat. Nos. 4,485,175 and No. 4,528,274 other than FIG. D of the former. Compared to FIG. D of U.S. Pat. No. 4,485,175, the shape of certain histograms obtained according to the present invention may render more feasible the identification of blood samples with abnormal distributions of basophils, eosinophils and monocytes. Nonetheless, the quantitation of these three leukocyte types with the resultant quantitative differentiation of leukocytes into all five types, is likely to require significant additional work.

An exemplary diluent used in the present invention has the composition shown below in Table I.

TABLE I

Exemplary Diluent Composition

| | |
|---|---|
| Sodium BES | 3.0 g/L |
| 50% Sodium Hydroxide | 0.46 |
| Sodium Chloride | 4.0 |
| Sodium Sulfate | 9.72 |
| Disodium EDTA | 0.03 |
| Urea | 0.5 |
| 37% Formaldehyde | 0.97 mL/L |
| Potassium Chloride | 0.03 g/L |
| Procaine Hydrochloride | 0.11 |
| Deionized Water | 995 |

In the above formulation, all ingredients are measured in grams per liter of total formulation except the formaldehyde. BES refers to the Good's Buffer N,N-Bis (2-hydroxyethyl)-2-aminoethane sulfonic acid. EDTA refers to ethylenediamine tetraacetic acid. Furthermore, the ingredient procaine hydrochloride may be omitted from the formulation for most applications.

Two preferred lysing reagents containing a benzyl compound are set forth in Tables II and III:

TABLE II

Lysing Reagent A

| | |
|---|---|
| Dodecyltrimethylammonium Chloride (95% solid) | 19 g/L |
| Benzyldimethyltetradecylammonium Chloride (95% solid) | 1.80 |
| Potassium cyanide | 0.25 |
| Isopropanol | 18 mL/L |
| Deionized water | 982 g/L |

TABLE III

Lysing Reagent B

| | |
|---|---|
| Dodecyltrimethylammonium Chloride (95% solid) | 69.14 g/L |
| Benzyldimethyltetradecylammonium Chloride (95% solid) | 4.97 |
| Potassium cyanide | 0.885 |
| Isopropanol | 35.4 mL/L |
| Deionized water | 882 g/L |

A suitable lysing reagent formulation containing a pyridinium compound is set forth in Table IV.

TABLE IV

Lysing Reagent C

| | |
|---|---|
| Dodecyltrimethylammonium Chloride | 19.0 g/L |
| Cetylpyridinium Chloride | 2.0-2.5 g/L |
| Potassium cyanide | 0.25 g/L |
| Isopropanol | 18 mL/L |
| Deionized water | 980 g/L |

In preparing each of the above formulations, the order of addition is not critical. Where isopropanol is used in the lysing reagent, its primary function is to enhance the solubility of the second cationic agent. Accordingly, it may be advantageous to premix such second cationic reagent with the isopropanol before adding it to the other ingredients. At the least, it is preferable to introduce the isopropanol before introducing either cationic agent.

The amounts of sodium hydroxide indicated in the above diluent formulation is illustrative. Normally, the sodium hydroxide is added, if at all, in an amount sufficient to bring each formulation to a target pH range (6.9-7.1 for the diluent, 10.0 to 10.2 for each lysing reagent). If any formulation is too basic, HCl may be added to achieve the desired pH.

In the diluent formulation shown in Table I, the buffer used was Sodium BES (a Goode's Buffer); other Goode's Buffers such as BIS/TRIS can also be used with similar results.

EXAMPLES

Example 1

A diluent was prepared as in Table I and a lysing reagent of formula A was prepared as in Table II. The two reagents were employed in a COULTER S PLUS IV instrument, modified by the manufacturer (Coulter electronics, Inc.) for three-part leukocyte differentiation. It is believed that, in operation, the instrument admixes 28 microliters of blood, 6.0 milliliters of diluent and 1.0 milliliters of lysing reagent in the manner described in U.S. Pat. No. 4,485,175 and, after approximately 3 seconds, initiates counting of white cells for approximately 7 seconds. The histograms of white cells wee displayed on a terminal/plotter. FIG. 1 illustrate one such histogram. As indicated by numerals L, M and G, distinct populations of lymphocytes, mononuclear cells and granulocyte were seen. These peaks were clearly differentiated by the valley to he right of peak L and the valley to the left of peak G.

EXAMPLE 2

A diluent was prepared as a Table I and a lysing reagent of formula B was prepared as in Table III. The two reagents were employed on a modified CELLECT instrument (from the Instrumentation Laboratory division o the present assignee Fisher Scientific company) which, in operation, introduces into the reaction chamber the following ingredients:

| | | |
|---|---|---|
| 1) Diluent | 0.911 ml | 0.458 sec |
| 2) Lyse | 0.370 ml | 0.186 |
| 3) Diluent | 4.657 ml | 2.34 |
| 4) Pause | | 1.25 |
| 5) Diluent | 0.569 ml | 0.286 |
| 6) Blood | 0.040 ml | 0.02 sec |
| 7) Diluent | 3.463 ml | 1.74 sec. |

Thus the final reaction mixture is made up of 0.040 ml blood, 0.370 ml lysing reagent of formula B and 9.6 ml of diluent of the formula shown in Table I.

Figure 2A:
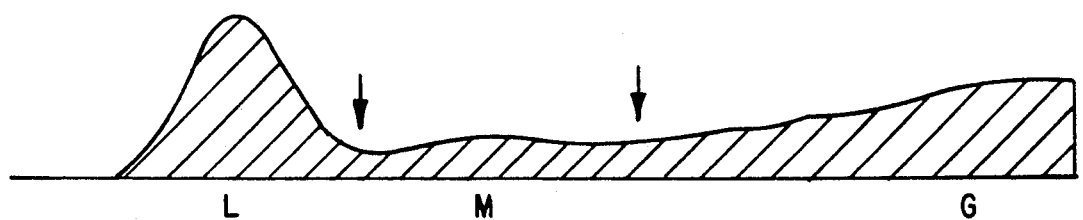
FIG. 2A is a garlic view of a histogram prepared using the lysing reagent of the preset invention of a blood sample with a normal leukocyte distribution in accordance with Example 2.

A representative histogram obtained by the CELLECT instrument and displayed ya video display is shown in FIG. 2A, wherein the blood sample wa of a normal leukocyte distribution. /Again, numerals L, M and G indicate three populations o leukocytes.

Figure 2B:
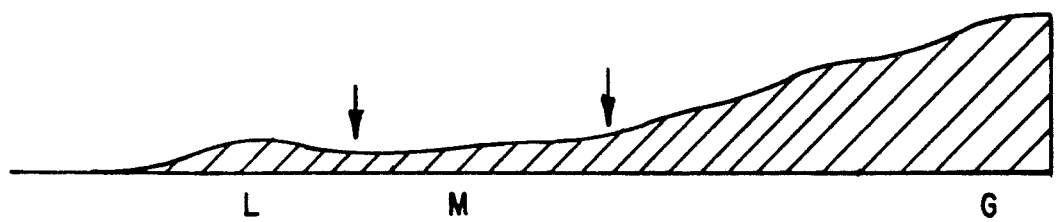
FIG. 2B is a graphic view similar o FIT. 2A of a histogram of a blood sample with an abnormal leukocyte distribution in accordance Example 2.
Figure 3:
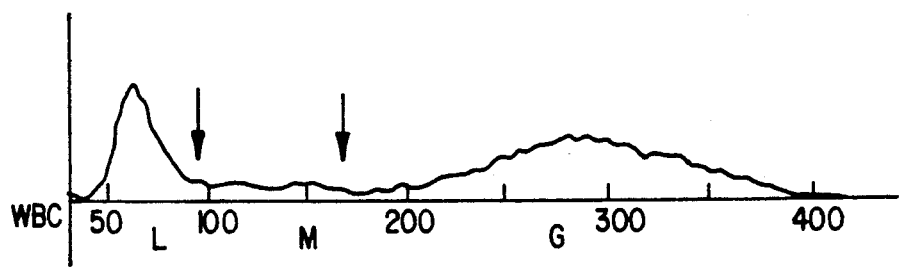
FIG. 3 is a graphic view similar to FIG. 1, using a lysing reagent in accordance with a different embodiment of the present invention on a Coulter S Plus IV instrument.

A representative histogram obtained by the CELLECT instrument wherein the blood sample was abnormal, being depleted of lymphocytes, is shown in FIG. 2B. Numerals L, M and G indicate three populations of leukocytes. By counting he particles in the thee populations (with he arrows in FIGS. 2A and 2B indicating where divisions were made), the proportions were as follows for the normal and abnormal samples:

| Leukocyte Population | % in FIG. 2A | % in FIG. 2B |
|---|---|---|
| Lymphocytes | 24.7 | 4.9 |
| Mononuclear | 6.3 | 2.8 |
| Granulocytes Neutrophils | 69.2 | 92.3. |

Furthermore, the shape of the mononuclear region M in FIGS. 2A and 2B is illustrative of the differences between normal and certain abnormal distributions.

EXAMPLE 3

A diluent was prepared as in Table 1 and lysing reagent was prepared as in the following Table V:

TABLE V

| Lysing Reagent D | |
| --- | --- |
| Dodecyltrimethylammonium Chloride (95% solid) | 62.80 g/L |
| Cetylpyridinium Chloride (95% solid) | 7.70 g/L |
| Potassium Cyanide | 0.885 g/L |
| Isopropanol | 50 mL/L |
| Deionized Water | 878 g/L |

Figure 4:
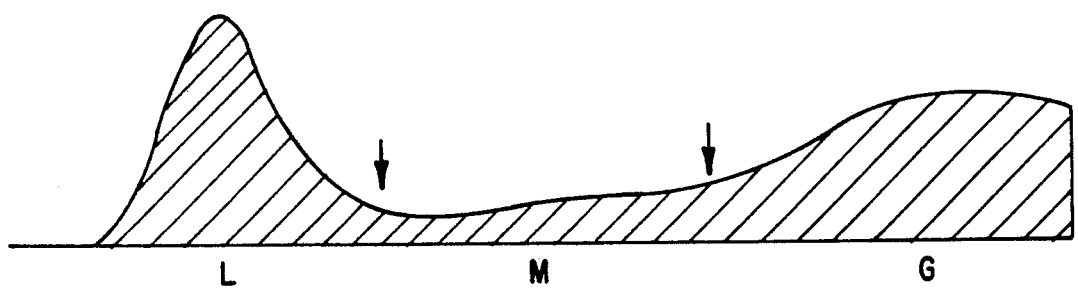
FIG. 4 is a graphic view similar to FIG. 2A of a histogram using a lysing reagent in accordance with a different embodiment of the present invention in accordance with Example 3.

These reagents were used on the modified CELLECT instrument in the manner described in Example 2. A representative histogram is shown in FIG. 4.

What is claimed is:

1. In a lysing reagent for use in automated hematological measurement being an aqueous solin containing dodecyltrimethyl ammonium halide and a second cationic agent, the improvement wherein the second cationic agent is selected from the group consisting of benzyltrialkylammonium halides of the formula:

$$Ph-CH_2-N^+(R)_2-Q\ X^-$$

and alkylpyridinium halides of the formula:

$$A=N^+Q\ x^-$$

wherein Ph is phenyl, R is methyl or ethyl, Q is alkyl of 14 to 16 carbons, A=N is pyridinium and X is chlorine or bromine.

2. The lysing reagent of claim 1 wherein the second cationic agent is a benzyltrialkylammonium halide.

3. The lysing reagent of claim 2 where X is chlorine in the formula for the benzyltrialkylammonium halide 4. The lysing reagent of claim 3 where R is methyl in each instance.

5. The lysing reagent of claim 4 wherein Q is tetradecyl, the second cationic agent being benzyltetradecyldimethylammonium chloride.

6. The lysing reagent of claim 2 further containing an alkanol of 2-6 carbons.

7. The lysing reagent of claim 6 wherein the alkanol is isopropanol

8. The lysing reagent of claim 1 wherein the first cationic reagent is dodecyltrimethylammonium chloride 9. The lysing reagent of claim 1 where the second cationic agent is an alkylpyridinium halide.

10. The lysing reagent of claim 9 wherein X in the formula for the alkylpyridinium halide is chlorine 11. The lysing reagent of claim 10 wherein Q is tetradecyl.

12. The lysing reagent of claim 10 wherein Q is hexadecyl.

13. In a method for stromatolyzing a blood sample by mixing with a solution of cationic agents to produce a reaction mixture in which the leukocytes have been differentiated by size into subpopulations, with one of the cationic agents being a dodecyltrimethylammonium halide, the improvement wherein another of the cationic agents is selected from the group consisting of benzyltrialkylammonium halides of the formula:

$$Ph-CH_2-N^+(R)_2-Q\ X^-$$

and alkylpyridinium halides of the formula:

$$A=N^+Q\ X^-$$

wherein Ph is phenyl, R is methyl or ethyl, Q is alkyl of 14 to 16 carbons, A=N is pyridinium and X is chlorine or bromine.

14. The method of claim 13 wherein the second cationic agent is a benzyltrialkylammonium halide 15. The method of claim 14 where X is chlorine in the formula for the benzyltrialkylammonium halide.

16. The method of claim 15 where R is methyl in each instance.

17. The method of claim 16 wherein Q is tetradecyl, the second cationic agent being benzyltetradecyldimethylammonium chloride 18. The method of claim 14 wherein the lysing reagent further contains an alkanol of 2-6 carbons 19. The method of claim 18 wherein the alkanol is isopropanol.

20. The method of claim 13 wherein the first cationic reagent is dodecyltrimethylammonium chloride.

21. The method of claim 13 where the second cationic agent is an alkylpyridinium halide 22. The method of claim 21 wherein X in the formula for the alkylpyridinium halide is chlorine.

23. The method of claim 22 wherein Q is tetradecyl.

24. The method of claim 22 wherein Q is hexadecyl.

25. The method of claim 13 wherein the lysing reagent is admixed with the major proportion of a diluent, and minor proportion of the diluent and a blood sample are then added to the mixture containing lysing reagent.

* * * * *